(12) United States Patent
Löfgren

(10) Patent No.: US 6,564,803 B2
(45) Date of Patent: May 20, 2003

(54) DISPOSABLE SURGICAL DRAPE

(75) Inventor: Kristina Löfgren, Mölnlycke (SE)

(73) Assignee: Molnlycke Health Care AB, Gothenburg (SE)

( * ) Notice: Subject to any disclaimer, the term of this patent is extended or adjusted under 35 U.S.C. 154(b) by 93 days.

(21) Appl. No.: 09/727,505

(22) Filed: Dec. 4, 2000

(65) Prior Publication Data

US 2002/0020418 A1 Feb. 21, 2002

(30) Foreign Application Priority Data

Dec. 10, 1999 (SE) ............................................. 9904525

(51) Int. Cl.⁷ ............................................... A61B 19/00
(52) U.S. Cl. ...................................................... 128/849
(58) Field of Search ................................... 128/849–856

(56) References Cited

U.S. PATENT DOCUMENTS

| | | | | |
|---|---|---|---|---|
| 3,677,266 A | * | 7/1972 | Green | 128/853 |
| 4,573,991 A | * | 3/1986 | Pierniak | 604/385 |
| 4,710,185 A | * | 12/1987 | Sneyd | 604/372 |
| 5,151,314 A | * | 9/1992 | Brown | 128/849 |

* cited by examiner

Primary Examiner—Michael A. Brown
(74) Attorney, Agent, or Firm—Burns, Doane, Swecker & Mathis, L.L.P.

(57) ABSTRACT

The present invention relates to a disposable surgical drape (1) that includes a layer (2) of absorbent material and a layer (3) of plastic material. According to the invention, net material (4) extends between the respective layers of absorbent material and plastic material (2 and 3) over the entire drape (1) or over parts thereof.

11 Claims, 1 Drawing Sheet

DISPOSABLE SURGICAL DRAPE

FIELD OF INVENTION

The present invention relates to a so-called disposable surgical drape that comprises a layer of absorbent material and a layer of plastic material.

BACKGROUND OF THE INVENTION

In the case of certain types of disposable surgical drapes, it is desirable to improve the burst strength of the drape, for instance so as to prevent the fingers of theatre personnel from making holes in an orthopaedic surgical drape when placing the drape around the patient. With other types of surgical drapes, it is desirable to improve the tear strength of the drape, for instance to prevent tearing of a slit drape at the end of the slit when handling the drape. One way of increasing the burst strength and tear strength of a drape is, of course, to increase the thicknesses of the drape layers, although this will result in a drape that is less pliant than would otherwise be the case, i.e. a drape that is less able to conform to the body contours of a patient.

An object of the present invention is to increase the burst strength and tear strength of a disposable surgical drape without seriously impairing the pliancy, i.e. the so-called drapability, of the drape, and also to enhance the liquid absorption capacity of the drape.

SUMMARY OF THE INVENTION

These objects are achieved in accordance with the invention with a disposable surgical drape that includes a layer of absorbent material and a layer of plastic material and that is characterised by net material which extends between the layers of absorbent material and plastic material either over the entire drape or over parts thereof.

In one preferred embodiment of the invention, the layers of absorbent material and plastic material are fastened to each other and to the net material by means of a sparse pattern of bonding lines or bonding points. The net material comprises longitudinally and transversely extending threads which are disposed in a chequered pattern and which are mutually spaced apart at a distance of less than 12 mm. The threads in the net material are comprised of synthetic fibres, such as polyester or nylon fibres, or textile fibres, such as cotton or rayon fibres, having a size smaller than 500 dtex.

BRIEF DESCRIPTION OF THE DRAWING

The invention will now be described with reference to FIG. 1 which illustrates in perspective part of a surgical drape according to a preferred embodiment of the invention, with part of the absorbent layer of the drape cut away.

DESCRIPTION OF ONE EMBODIMENT

Figure 1:
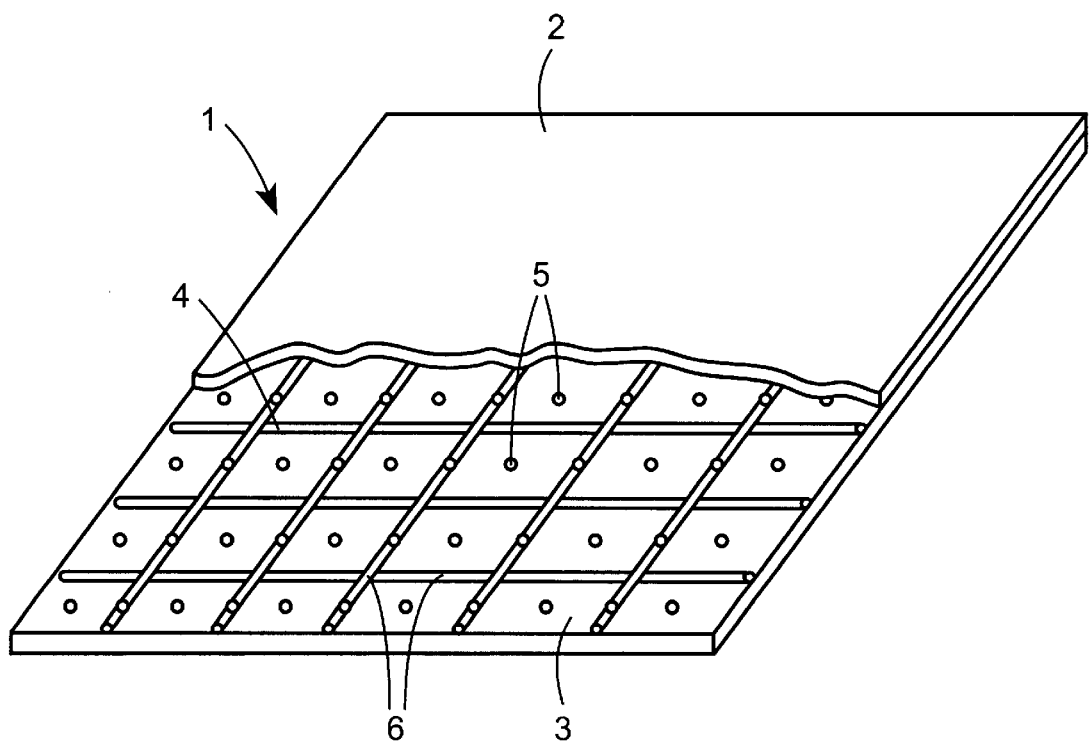

As shown in FIG. 1 is a surgical drape 1 that comprises an upper layer 2 of absorbent material, a lower plastic layer 3, and a layer of net material 4 disposed between the layers 2 and 3. The layers 2 and 3 are bonded together by a sparse pattern of glue points 5, as shown schematically in the Figure.

The absorbent material 2 is a nonwoven material comprised of absorbent fibres, for instance viscose fibres, although other fibre materials, such as polyolefins can be used. The plastic layer 3 is comprised of polyethylene, although other plastic materials, such as polyolefins can be used.

The net material is comprised of threads 6 of polyester having a size of 280 dtex. Threads of other synthetic fibres, such as nylon fibres, or of cotton fibres or rayon fibres, for instance, may alternatively be used.

The glue 5 may be a water-based EVA glue, although hot melt glues and acrylate glues may be used. The glue pattern may be different to that shown in the Figure and need not be a regular pattern.

The threads 6 are disposed in a chequered pattern in the case of the illustrated embodiment. In order to impart the requisite burst strength to the drape, the local distance between the threads may not be greater than 12 mm. This will ensure that the fingers of theatre personnel will always press against or be in contact with at least two threads when draping the drape around a patient. In order that the threads will not stiffen the drape to an extent which will seriously detract from the desired pliancy of the drape, the distance between respective longitudinally and transversely extending threads should not be less than 2 mm. The threads will preferably have a coarseness of less than 500 dtex.

Because the net material 4 is solely joined to the sheets 2 and 3 in a punctiform fashion, the net has a far less stiffening effect on the drape than if the threads 6 in the net material bonded to the layers 2 and/or 3 along the whole of their lengths.

The net material 4 need not extend over the entire surface of the drape 1, as it is sufficient to dispose net material on selected areas of the drape, for instance at that part of an orthopaedic drape which is grasped by theatre personnel when arranging the drape about a patient, or at the ends of the slit of a slit drape. Naturally, the net material may be allowed to extend over the entire drape. In the case of such a drape construction, one or both layers 2, 3 of the drape 1 may be made thinner than would otherwise be the case, as the net material will also enhances the tensile strength of the drape.

By dimensioning and bonding net material in the aforedescribed manner, it is possible to improve the burst strength and tear strength of a surgical drape in accordance with the invention in a simple and effective manner, without jeopardising the so-called drapability of the drape. The absorption capacity of the drape is also enhanced, by virtue of the fact that liquid can be stored in the cavities formed by distancing the upper sheet 2 locally from the lower sheet 3, by means of the threads 6.

It will be understood that the described embodiment can be modified within the scope of the invention. For instance, the drape may be provided with a soft bottom layer, to improve user comfort. Furthermore, the glue pattern may be comprised of glue strings instead of glue points. Moreover, the drape layers and net material may be joined together by linear or spot welding. The squares in the chequered pattern of the net material may be rectangular (oblong) or rhombic instead of square, even though squares are preferred. The scope of the invention is therefore restricted solely by the content of the accompanying Claims.

What is claimed is:

1. A disposable surgical drape that comprises a layer of absorbent material and a layer of plastic material and that is characterised by net material that extends between the layers of absorbent material and plastic material.

2. A surgical drape according to claim 1, wherein the layers of absorbent material and plastic material are bonded to each other and to the net material by means of a sparse pattern of bonding lines or bonding points.

3. A surgical drape according to claim 2, wherein the net material is comprised of longitudinally and transversely extending threads that form a chequered pattern; and the longitudinally and transversely extending threads are spaced apart at a distance of less than 12 mm.

4. A surgical drape according to claim 2, wherein the net material extends between the layers over the entire drape.

5. A surgical drape according to claim 2, wherein the net material extends between the layers at only selected areas of the drape.

6. A surgical drape according to claim 1, wherein the net material is comprised of longitudinally and transversely extending threads that form a chequered pattern; and the longitudinally and transversely extending threads are spaced apart at a distance of less than 12 mm.

7. A surgical drape according to claim 6, wherein the threads in the net material comprise synthetic fibres, such as polyester or nylon fibres, or textile fibres, such as cotton fibres or rayon fibres and have a coarseness that is less than 500 dtex.

8. A surgical drape according to claim 6, wherein the net material extends between the layers over the entire drape.

9. A surgical drape according to claim 6, wherein the net material extends between the layers at only selected areas of the drape.

10. A surgical drape according to claim 1, wherein the net material extends between the layers over the entire drape.

11. A surgical drape according to claim 1, wherein the net material extends between the layers at only selected areas of the drape.

* * * * *